(12) United States Patent
Yahata et al.

(10) Patent No.: US 11,305,986 B2
(45) Date of Patent: Apr. 19, 2022

(54) METHOD OF MANUFACTURING SEMICONDUCTOR DEVICE, SUBSTRATE PROCESSING APPARATUS AND PROGRAM

(71) Applicant: KOKUSAI ELECTRIC CORPORATION, Tokyo (JP)

(72) Inventors: Takashi Yahata, Toyama (JP);
Naofumi Ohashi, Toyama (JP);
Tadashi Takasaki, Toyama (JP)

(73) Assignee: KOKUSAI ELECTRIC CORPORATION, Tokyo (JP)

( * ) Notice: Subject to any disclaimer, the term of this patent is extended or adjusted under 35 U.S.C. 154(b) by 247 days.

(21) Appl. No.: 16/797,322

(22) Filed: Feb. 21, 2020

(65) Prior Publication Data
US 2020/0346924 A1 Nov. 5, 2020

(30) Foreign Application Priority Data
Feb. 21, 2019 (JP) .............................. JP2019-029583

(51) Int. Cl.
| | |
|---|---|
| *H01L 21/02* | (2006.01) |
| *C23C 16/40* | (2006.01) |
| *B81C 1/00* | (2006.01) |
| *C23C 16/34* | (2006.01) |
| *C23C 16/50* | (2006.01) |
| *H01J 37/32* | (2006.01) |

(52) U.S. Cl.
CPC ........ *B81C 1/00158* (2013.01); *C23C 16/345* (2013.01); *C23C 16/401* (2013.01); *C23C 16/50* (2013.01); *H01J 37/32082* (2013.01); *H01J 37/32449* (2013.01); *H01L 21/0217* (2013.01); *H01L 21/02164* (2013.01); *H01L 21/02274* (2013.01); *H01J 2237/3321* (2013.01)

(58) Field of Classification Search
None
See application file for complete search history.

(56) References Cited

U.S. PATENT DOCUMENTS

| | | | |
|---|---|---|---|
| 2017/0291192 A1 | 10/2017 | Machida et al. | |
| 2019/0057862 A1* | 2/2019 | Yang | .................. H01L 21/02274 |
| 2019/0062918 A1* | 2/2019 | Shaikh | .............. C23C 16/45519 |
| 2019/0385907 A1* | 12/2019 | Gottheim | ............ H01L 21/6831 |

FOREIGN PATENT DOCUMENTS

JP        2016-72661 A        5/2016

* cited by examiner

*Primary Examiner* — Asok K Sarkar
(74) *Attorney, Agent, or Firm* — Oliff PLC

(57) ABSTRACT

There is provided a technique for improving a resistance of a film to vibration in a semiconductor device having a vibrating film, including at least: forming a first silicon oxide film; forming a first silicon nitride film; forming a second silicon oxide film; and forming a second silicon nitride film, and each film formation is performed using a substrate processing apparatus configured to supply gas to a process chamber including upper and bottom electrodes, and selectively supply high frequency power or low frequency power to each of the upper and bottom electrodes by switching.

20 Claims, 8 Drawing Sheets

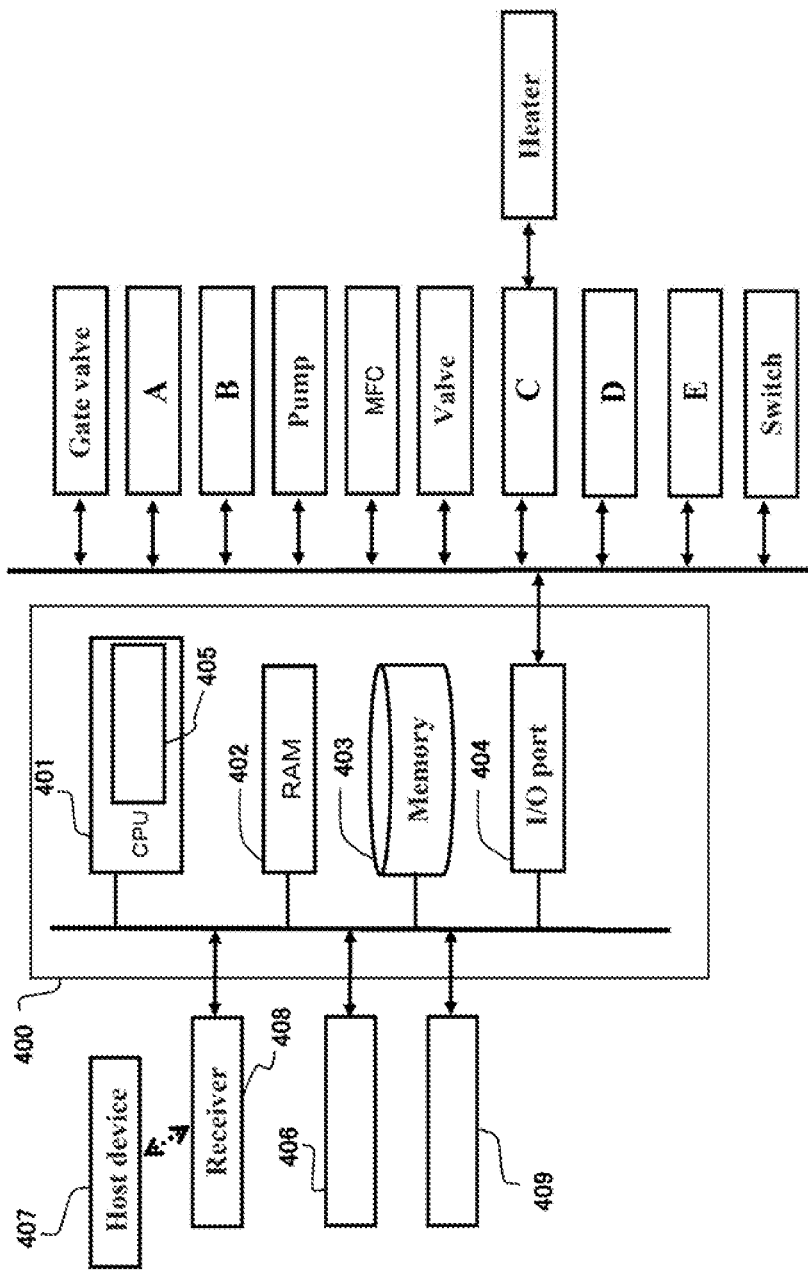

S206 Is each formation performed predetermined number of times?

S208 Does an uppermost layer have the same composition as the composition of a coating film?

METHOD OF MANUFACTURING SEMICONDUCTOR DEVICE, SUBSTRATE PROCESSING APPARATUS AND PROGRAM

TECHNICAL FIELD

The present disclosure relates to a method for manufacturing a semiconductor device, a substrate processing apparatus, and a non-transitory computer readable recording medium.

BACKGROUND

In recent years, an ultrasonic diagnostic apparatus that diagnoses an inside of a human body with ultrasonic waves has been used. A CMUT device (Capacitive Micromachined Ultrasonic Transducer) that functions as an ultrasonic transducer is used for the ultrasonic diagnostic apparatus. The CMUT device is formed by a MEMS (Micro Electro Mechanical System) technique, which is a kind of a semiconductor manufacturing technique, and is configured to include a vibrating film with a membrane structure, and radiate ultrasonic waves to the outside or detect ultrasonic waves from the outside by vibrating the vibrating film (see, for example, Patent Document 1).

[Patent Document 1] Japanese Unexamined Patent Publication No. 2016-072661

SUMMARY

There is a problem in the CMUT device such that the membrane structure supporting the vibrating film may deteriorate, due to repeated vibration of the vibrating film. Deterioration of the membrane structure may cause a contact between counter electrodes due to bending of the vibrating film, which may lead to a failure of the CMUT device.

The present disclosure provides a technique for improving a resistance of the film to vibration in a semiconductor device having a film that vibrates like the CMUT device.

According to an aspect of the present disclosure, there is provided a technique, including at least:
  forming a first silicon oxide film;
  forming a first silicon nitride film;
  forming a second silicon oxide film; and
  forming a second silicon nitride film,
as a formation of the insulating film,
  the formation of the second silicon oxide film including:
  supplying silicon-containing gas and oxygen-containing gas to a process chamber; and
  performing switching to supply low frequency power to a top electrode installed in the process chamber, and supply high frequency power to a bottom electrode installed in the process chamber, and
  the formation of the second silicon nitride film including:
  supplying silicon-containing gas and nitrogen-containing gas to the process chamber; and
  performing switching to supply low frequency power to the top electrode and supply high frequency power to the bottom electrode.

According to the technique of the present disclosure, there is provided a semiconductor device including a vibrating film capable of improving a resistance to its vibration.

BRIEF DESCRIPTION OF THE DRAWINGS

FIG. 4 is a block diagram schematically illustrating a configuration example of a controller included in the substrate processing apparatus according to an embodiment of the present disclosure.

DETAILED DESCRIPTION

Embodiment

Embodiments of the present disclosure will be described hereafter, with reference to the drawings.
(1) Configuration of Semiconductor Device First, explanation will be given for a semiconductor device to which the technique according to the present disclosure is applied. In the present embodiment, a CMUT device, which is a type of a semiconductor device, is taken as an example.

The CMUT device has a membrane structure (CMUT cell) formed on a substrate by MEMS technique, and may have a single cell structure or an array structure in which a large number of cells are arranged. The CMUT device having a single cell structure will be described hereafter, as an example.

Figure 1:
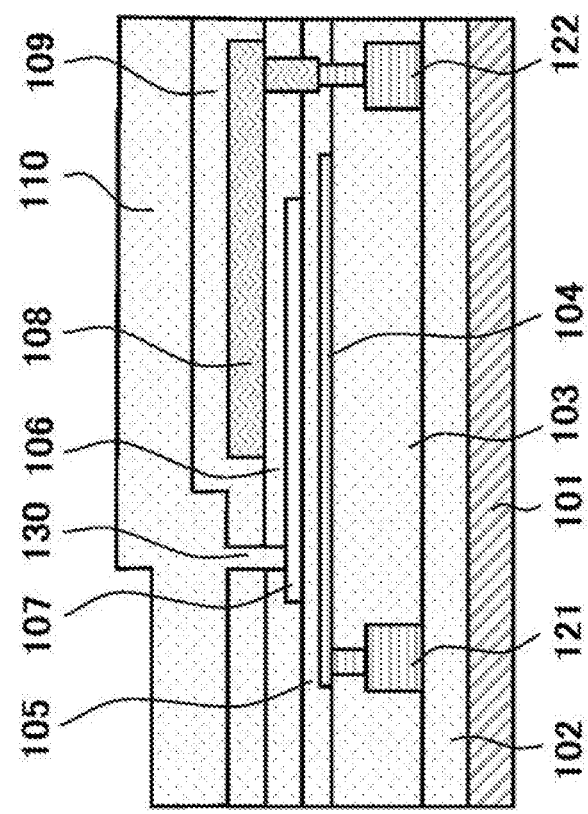
FIG. 1 is a sectional view illustrating a configuration example of a CMUT device which is a kind of a semiconductor device.

FIG. 1 is a sectional view illustrating a configuration example of a CMUT device which is one type of a semiconductor device.

As illustrated in FIG. 1, in the CMUT device, a bottom electrode 104 is formed on an upper layer of a substrate 101 interposing insulating films 102 and 103, and a cavity 107 surrounded by insulating films 105 and 106 is formed on further upper layer. Further, a top electrode 108 is formed above the cavity 107 at a position overlapping the cavity 107 interposing the insulating film 106. In addition, insulating films 109 and 110 are formed on an upper layer of the top electrode 108.

As described above, in the CMUT device, the bottom electrode 104 and the top electrode 108 that configures a pair of electrode films are arranged to face each other interposing the cavity 107. The bottom electrode 104 is connected to a wiring 121 formed on an upper surface of the insulating film 102. Also, the top electrode 108 is connected to a wiring 122 formed on the upper surface of the insulating film 102.

Thereby, a voltage can be applied or a change in capacitance can be detected between the bottom electrode 104 and the top electrode 108.

Further, a hole 130 is formed in the insulating films 106 and 109 formed above the cavity 107 so as to penetrate these films. The hole 130 functions as an etching hole for forming the cavity 107, and is embedded by the insulating film 110 after the cavity 107 is formed.

In the CMUT device with such a configuration, the insulating films 106, 109, 110 and the top electrode 108 formed above the cavity 107 are supported to be freely vibrated, thereby forming a membrane structure. That is, the top electrode 108 and the insulating films 106, 109, 110 attached thereto function as vibrating films with a membrane structure, and in the CMUT device, for example, when a voltage is applied between the bottom electrode 104 and the top electrode 108, an electrostatic force acts to vibrate the vibrating films at a frequency of the applied voltage, thereby transmitting ultrasonic waves. Conversely, in the case of reception, when the vibrating films vibrate due to a pressure of the ultrasonic waves from outside, a distance between the bottom electrode 104 and the top electrode 108 changes, and therefore the ultrasonic waves can be detected as a change in capacitance.

(2) Configuration of a Substrate Processing Apparatus

A substrate processing apparatus used for manufacturing the CMUT device with the above-described configuration will be described next.

The substrate processing apparatus described in the present embodiment is used in manufacture of a semiconductor device, and is configured as a single-wafer type substrate processing apparatus that processes substrates to be processed one by one. The substrate includes, for example, a semiconductor wafer (simply referred to as "wafer" hereafter). Further, processing performed by the substrate processing apparatus includes, for example, oxidation processing, diffusion processing, reflow and annealing for carrier activation and flattening after ion implantation, and film forming processing. In the present embodiment, a case of performing a film forming processing will be described as an example.

A configuration of the substrate processing apparatus will be specifically described hereafter, with reference to the drawings.

Figure 2:
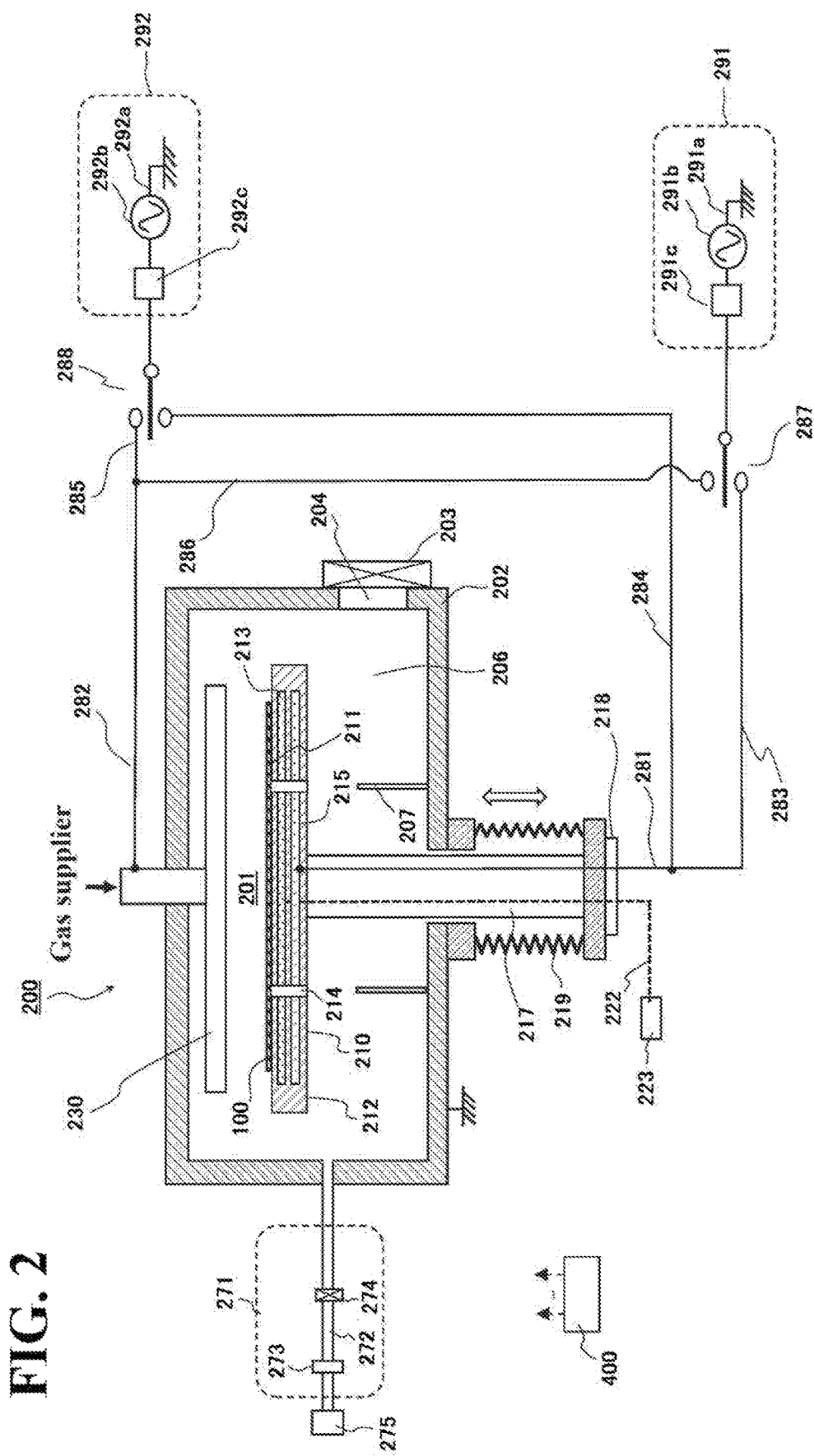
FIG. 2 is a side sectional view schematically illustrating a schematic configuration example of a substrate processing apparatus according to an embodiment of the present disclosure.
Figure 3A:
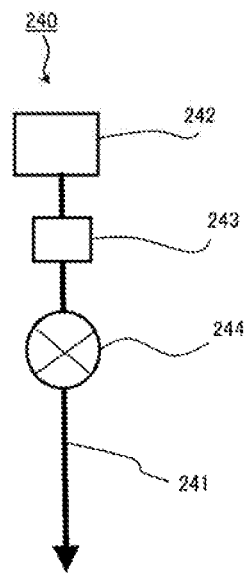
FIGS. 3A, 3B, and 3C are block diagrams schematically illustrating a configuration example of a gas supplier included in the substrate processing apparatus according to an embodiment of the present disclosure.
Figure 3B:
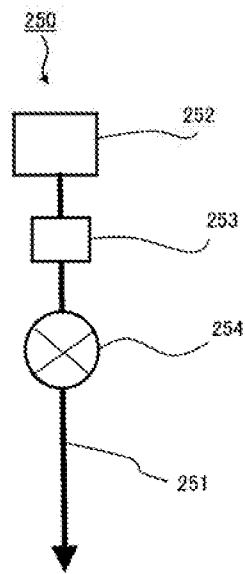
Figure 3C:
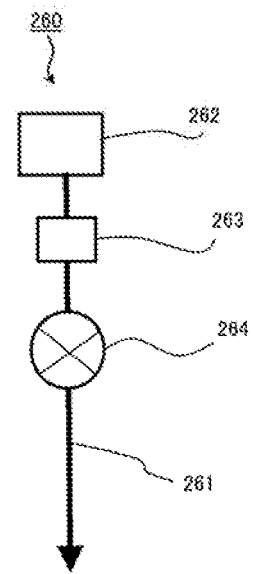

FIG. 2 is a side sectional view schematically illustrating a schematic configuration example of a substrate processing apparatus according to the present embodiment, and FIGS. 3A, 3B, and 3C are block diagrams schematically illustrating a configuration example of a gas supplier included in the substrate processing apparatus according to the present embodiment, and FIG. 4 is a block diagram schematically illustrating a configuration example of a controller included in the substrate processing apparatus according to the present embodiment.

(Processing Container)

As illustrated in FIG. 2, a substrate processing apparatus 200 includes a processing container (container) 202. The container 202 has, for example, a circular cross section and is configured as a flat airtight container. Further, the container 202 is made of a metal material such as aluminum (Al) or stainless steel (SUS). A process chamber 201 for processing a substrate 100 such as a silicon wafer, and a transfer space 206 through which the substrate 100 passes when the substrate 100 is transferred to the process chamber 201, are formed in the container 202.

A substrate loading/unloading port 204 adjacent to a gate valve 203 is provided on a side surface of the container 202, so that the substrate 100 moves to and from a transfer chamber (not illustrated), through the substrate loading/unloading port 204. A plurality of lift pins 207 are provided on a bottom of the container 202.

A substrate support 210 that supports the substrate 100 is disposed in the process chamber 201. The substrate support 210 mainly includes: a substrate mounting surface 211 on which the substrate 100 is mounted, a substrate mounting table 212 with the substrate mounting surface 211 on its surface, a heater 213 as a heating source provided in the substrate mounting table 212, and a bottom electrode 215. Through-holes 214 through which the lift pins 207 pass are formed in the substrate mounting table 212 at positions corresponding to the lift pins 207, respectively. A heater controller 223 that controls a temperature of the heater 213 is connected to the heater 213 via a communication line 222, for heating to a desired temperature according to an instruction from a controller 400 described later. A wiring 281 is electrically connected to the bottom electrode 215.

The substrate mounting table 212 is supported by a shaft 217. The shaft 217 penetrates the bottom of the processing container 202, and further, is connected to a lifter 218 outside the processing container 202. Then, by operating the lifter 218 and moving up and down the shaft 217 and the substrate mounting table 212, the substrate mounting table 212 can move up and down the substrate 100 mounted on the mounting surface 211. The shaft 217 is insulated from the processing container 202. Further, the periphery of a lower end portion of the shaft 217 is covered with bellows 219, so that an inside of the process chamber 201 is kept airtight.

When the substrate 100 is transferred, the substrate mounting table 212 moves down to a position facing the substrate loading/unloading port 204, and when the substrate 100 is processed, as illustrated in FIG. 1, the substrate 100 moves up to a processing position in the process chamber 201.

A shower head 230 used as a top electrode is provided on the upper side (upstream side) of the process chamber 201. The shower head 230 communicates with a gas supplier described later and has a role of supplying the supplied gas to the process chamber 201. A wiring 282 described below is electrically connected to the shower head 230.

(Gas Supplier)

The gas supplier is configured to communicate with the shower head 230. As illustrated in FIGS. 3A, 3B and 3C, the gas supplier includes: a first gas supplier 240, a second gas supplier 250, and a third gas supplier 260.

(First Gas Supplier)

As illustrated in FIG. 3A, the first gas supplier 240 includes a first gas supply pipe 241 that communicates with the shower head 230.

The first gas supply pipe 241 is provided with a first gas source 242, a mass flow controller (MFC) 243 that is a flow rate controller (flow rate controller), and a valve 244 that is an open/close valve, in an order from an upstream direction.

The first gas source 242 is a supply source of a first gas containing a first element (also referred to as "first element-containing gas" hereafter). The first element-containing gas is a source gas containing the first element and is one of the processing gases.

Here, the first element is silicon (Si). That is, the first element-containing gas is a silicon-containing gas. Specifically, for example, tetraethoxysilane ($Si(OC_2H_5)_4$: TEOS) gas, monosilane ($SiH_4$) gas, dichlorosilane ($SiH_2Cl_2$: DCS) gas, hexachlorodisilane ($Si_2Cl_6$: HCDS) gas, etc., are used as the silicon-containing gas.

A first gas supplier (also referred to as "silicon-containing gas supplier" hereafter) 240 is mainly configured by a first gas supply pipe 241, MFC 243, and a valve 244.

(Second Gas Supplier)

As illustrated in FIG. 3B, the second gas supplier 250 includes a second gas supply pipe 251 that communicates with the shower head 230.

The second gas supply pipe 251 is provided with a second gas source 252, a flow rate controller (flow rate controller) MFC 253, and a valve 254 which is an open/close valve in an order from an upstream direction.

The second gas source 252 is a supply source of a second gas containing a second element (also referred to as "second element-containing gas" hereafter). The second element-containing gas is one of the processing gases. The second element-containing gas may be considered as a reaction gas.

Here, the second element-containing gas contains a second element different from the first element. The second element is oxygen (O). That is, the second element-containing gas is an oxygen-containing gas. Specifically, for example, oxygen ($O_2$) gas is used as the oxygen-containing gas.

The second gas supplier (also referred to as "oxygen-containing gas supplier" hereafter) 250 is mainly configured by a second gas supply pipe 251, MFC 253, and a valve 254.

(Third Gas Supplier)

As illustrated in FIG. 3C, the third gas supplier 260 includes a third gas supply pipe 261 that communicates with the shower head 230.

The third gas supply pipe 261 is provided with a third gas source 262, a flow rate controller (flow rate controller) MFC 263, and a valve 264 which is an open/close valve in an order from an upstream direction.

The third gas source 262 is a supply source of a third gas containing a third element (also referred to as "third element-containing gas" hereafter). The third element-containing gas is one of the processing gases. The third element-containing gas may be considered as a reaction gas or an inert gas.

Here, the third element-containing gas contains a third element different from both the first element and the second element. The third element is nitrogen (N). That is, the third element-containing gas is a nitrogen-containing gas. Specifically, for example, ammonia ($NH_3$) gas, nitrogen ($N_2$) gas or the like is used as the nitrogen-containing gas.

The third gas supplier (also referred to as "nitrogen-containing gas supplier" hereafter) 260 is mainly configured by a third gas supply pipe 261, MFC 263, and a valve 264.

When $N_2$ gas as the nitrogen-containing gas is supplied from the third gas supplier 260, the $N_2$ gas (inert gas) may act as a purge gas for purging the gas remaining in the container 202 and the shower head 230 in processing the substrate.

One of the first gas supplier 240, the second gas supplier 250, and the third gas supplier 260 described above, or a combination thereof is called a gas supplier or a gas supply system.

(Exhauster)

As illustrated in FIG. 2, an exhauster that exhausts an atmosphere in the container 202 includes an exhaust pipe 272 connected to the container 202, to communicate with the process chamber 201.

The exhaust pipe 272 is provided with APC (Auto Pressure Controller) 273, which is a pressure controller that controls an inside of the process chamber 201 to a predetermined pressure. The APC 273 includes a valve body (not illustrated) whose opening degree can be adjusted, and adjusts a conductance of the exhaust pipe 272 according to an instruction from a controller 400 described later. Further, in the exhaust pipe 272, a valve 274 is provided on an upstream side of the APC 273. The exhaust pipe 272, the valve 274, and the APC 273 are collectively referred to as an exhauster 271.

Further, the exhaust pipe 272 is provided with a dry pump (DP) 275. The DP 275 exhausts an atmosphere in the process chamber 201 through the exhaust pipe 272.

(Plasma Generator)

Further, as illustrated in FIG. 2, the wiring 281 connected to the bottom electrode 215 of the substrate support 210 is branched into a wiring 283 and a wiring 284. Then, one end of the wiring 283 is connected to a switch 287, and one end of the wiring 284 is connected to a switch 288.

On the other hand, the wiring 282 connected to the shower head 230 used as the top electrode is branched into a wiring 285 and a wiring 286. Then, one end of the wiring 285 is connected to the switch 288, and one end of the wiring 286 is connected to the switch 287.

The switch 287 is connected to a low frequency power supplier 291 in addition to the wirings 283 and 286.

The low frequency power supplier 291 supplies low frequency power to the shower head 230 or the bottom electrode 215. Therefore, the low frequency power supplier 291 includes a wiring 291a connected to the switch 287. The wiring 291a is provided with a low frequency power source 291b and a matching box 291c in an order from an upstream side. The low frequency power source 291b is connected to the ground.

Here, the low frequency means, for example, about 1 to 500 KHz, preferably about 250 to 400 KHz.

The switch 288 is connected to a high frequency power supplier 292, in addition to the wirings 284 and 285.

The high frequency power supplier 292 supplies high frequency power to the shower head 230 or the bottom electrode 215. Therefore, the high frequency power supplier 292 includes a wiring 292a connected to the switch 287. The wiring 292a is provided with a high frequency power source 292b and a matching box 292c in an order from an upstream side. The high frequency power source 292b is connected to the ground.

Here, the high frequency means, for example, about 13.56 MHz.

A Plasma generator in the present embodiment is mainly configured by the low frequency power supplier 291, the high frequency power supplier 292, and the switches 287 and 288.

In the plasma generator with such a configuration, a supply destination of the low frequency power by the low frequency power supplier 291 is switched to either the shower head 230 or the bottom electrode 215, by switching by the switch 287. Also, a supply destination of the high frequency power by the high frequency power supplier 292 is switched to either the shower head 230 or the bottom electrode 215, by switching by the switch 288.

The switching (that is, selection of the power supply destination) by the switches 287 and 288 is performed according to an instruction from a controller 400 described later.

(Controller)

The substrate processing apparatus 200 includes a controller 400 as a controller that controls an operation of each part of the substrate processing apparatus 200.

As illustrated in FIG. 4, the controller 400 is configured as a computer including at least: CPU (Central Processing Unit) 401 as a calculator; RAM (Random Access Memory)

402 as a temporary memory; a memory 403 such as a HDD (Hard Disk Drive) as a large-capacity memory; and I/O port 404.

Further, the controller 400 is configured so that an external memory 406 and an input/output device 409 such as a touch panel can be connected thereto. Moreover, a network can be connected to the controller 400 through a receiver 408. This means that the controller 400 can also be connected to a host device 407 such as a host computer existing on the network.

Further, the controller 400 is connected to each configuration of the substrate processing apparatus 200 via the I/O port 404, and reads a control program that controls an operation of the substrate processing apparatus 200, a process recipe that describes a substrate processing procedure and conditions, and the like, from the memory 403, according to an instruction from the host device 407 or an user, and gives an operation instruction depending on its content, to each configuration such as the switches 287, 288, the low frequency power supplier 291, and the high frequency power supplier 292. Transmission/reception control of the operation instruction is performed by, for example, a transmission/reception commander 405 in the CPU 401.

The process recipe is a combination that allows the controller 400 to perform each procedure in processing the substrate and obtain a predetermined result, and functions as a program. The process recipe, the control program, and the like are collectively referred to simply as a program hereafter. When the term, program, is used in this specification, only the process recipe alone may be included, only the control program alone may be included, or both may be included.

The controller 400 as described above may be configured as a dedicated computer or a general-purpose computer. For example, the controller 400 according to the present embodiment may be configured in such a way that an external memory storing the above program (for example, a magnetic tape, a magnetic disk such as a flexible disk and a hard disk, an optical disk such as CD and DVD, a magneto-optical disk such as MO, USB memory (USB Flash Drive), semiconductor memory such as a memory card) 406 is prepared, and using this external memory 406, the program is installed on the general-purpose computer. Further, the means for supplying the program to the computer is not limited to the case of supplying the program via the external memory 406. For example, communication means such as the Internet or a dedicated line may be used, or information may be received from the host device 407 via the receiver 408, and the program may be supplied without using the external memory 406. Moreover, instruction may be given to the controller 400 using the input/output device 409 such as a keyboard or a touch panel.

The memory 403 in the controller 400 and the external memory 406 connectable to the controller 400 are configured as a non-transitory computer-readable recording medium. These are collectively referred to as a non-transitory computer-readable recording medium hereafter. When the term, non-transitory computer-readable recording medium, is used in this specification, the memory 403 alone may be included, the external memory 406 alone may be included, or both may be included.

(3) Method for Manufacturing Semiconductor Device

Next, a method for manufacturing a semiconductor device, which is performed using the substrate processing apparatus 200 having the above-described configuration, will be described by taking a case of manufacturing a CMUT device as an example.

(Outline of a Procedure for Forming a CMUT Device)

First, an outline of a procedure for forming a CMUT device will be described, with reference to FIG. 1.

When forming the CMUT device, for example, an insulating film 102 including a silicon oxide film having a thickness of 400 nm (the silicon oxide film is also referred to as "SiO film" hereafter) is formed on a semiconductor substrate 101 by a plasma CVD (Chemical Vapor Deposition) method. Then, wirings 121 and 122 are formed on the insulating film 102 by a laminated film of titanium nitride and aluminum alloy, then, an insulating film 103 including, for example, a 500 nm-thick SiO film is formed by plasma CVD so as to cover the wirings 121 and 122. Further, an opening that reaches the wirings 121 and 122 are formed in the insulating film 103 by a lithography technique and a dry etching technique.

Thereafter, a conductive film to be the bottom electrode 104 is formed by a sputtering method. At this time, the opening of the insulating film 103 is also embedded. Then, an electrical connector to the bottom electrode 104 and the top electrode 108 is formed by the lithography technique and the dry etching technique. The conductive film to be the bottom electrode 104 may be a laminated film of titanium nitride and an aluminum alloy, or may be tungsten (W), titanium (Ti), aluminum (Al), copper (Cu), their alloys, nitrides, silicon compounds or the like which are used in a normal semiconductor process. The conductive film may have a thickness of, for example, about 100 nm. Then, the insulating film 105 including the SiO film is deposited on the bottom electrode 104 by plasma CVD to have a thickness of 200 nm, for example.

Next, an amorphous silicon film is deposited on an upper surface of the insulating film 105 by plasma CVD to have a thickness of 100 nm, subsequently, the amorphous silicon film is processed by lithography technique and dry etching technique, to thereby form a sacrificial layer to be the cavity 107 in a subsequent process. After forming the sacrificial layer, subsequently, the insulating film 106 including the SiO film is deposited by plasma CVD to have a thickness of 200 nm, for example, so as to cover the sacrificial layer and the insulating film 105. Then, an opening for connecting to the top electrode 108 are formed in the insulating films 105 and 106 by the lithography technique and the dry etching technique.

Thereafter, a conductive film to be the top electrode 108 is formed by a sputtering method. At this time, the opening in the insulating films 105 and 106 are also embedded. Then, the top electrode 108 is formed by the lithography technique and the dry etching technique. The conductive film to be the top electrode 108 may be a laminated film of titanium nitride and an aluminum alloy, or may be W, Ti, Al, Cu, their alloys, nitrides, silicon compounds or the like used in a normal semiconductor process. The conductive film is formed to have a thickness of about 400 nm, for example.

Then, after forming the top electrode 108, an insulating film 109 including a silicon nitride film (the silicon nitride film is also referred to as "SiN film" hereafter) is deposited by plasma CVD method to have a thickness of 300 nm, so as to cover the insulating film 106 and the top electrode 108. Subsequently, a hole 130 that reaches the sacrificial layer is formed in the insulating films 106 and 109, using the lithography technique and the dry etching technique.

Thereafter, the cavity 107 is formed by etching away the sacrificial layer with xenon fluoride gas ($XeF_2$) through the hole 130. After forming the cavity 107, the insulating film 110 is deposited by plasma CVD to have a thickness of 800 nm, for example, to embed the hole 130 used for forming the cavity 107.

Through such a procedure, the CMUT device with the above-described configuration can be formed.

(Procedure for Manufacturing Membrane-Forming Film)

Next, in the CMUT device with the above-described configuration, a procedure for forming a film that configures a vibrating film (membrane) will be described in detail.

Here, the case of forming the insulating film 110 as one of the membrane-forming film will be described as an example. However, the procedure described below can be applied to a case of forming not only the insulating film 110 but also other insulating films 105, 106 and 109.

The insulating film 110 is formed using the substrate processing apparatus 200 with the above-described configuration. In such a case, the substrate processing apparatus 200 performs substrate processing described below, to the substrate 100 that is a workpiece housed in the process chamber 201. The substrate processing includes at least loading a substrate, forming a film, and unloading the substrate. In the following description, the operation of each configuration of the substrate processing apparatus 200 is controlled by the controller 400.

(Substrate Loading)

In loading the substrate, the substrate 100 which is a workpiece, with the insulating film 109 formed on the semiconductor substrate 101, and the cavity 107 formed by etching the sacrificial layer through the hole 130, is loaded into the process chamber 201. Specifically, after loading the substrate 100 into the container 202 through the substrate loading/unloading port 204, the substrate 100 is mounted on the mounting surface 211 of the substrate mounting table 212, and further, the substrate support 210 is moved up to position the substrate 100 at a processing position (substrate processing position) in the process chamber 201.

Then, the inside of the process chamber 201 is exhausted through the exhaust pipe 272 so that the inside of the process chamber 201 is set in a desired pressure (vacuum degree). Thereby, the pressure in the process chamber 201 is maintained to a high vacuum of, for example, $10^{-5}$ to $10^{-1}$ Pa.

Further, an amount of electricity supplied to the heater 213 is feedback-controlled so that the inside of the process chamber 201 reaches a desired temperature. The temperature at this time is, for example, room temperature or more and 800° C. or less, preferably room temperature or more and 500° C. or less.

Thus, the preparation before the film formation is completed.

(Film Formation)

After the substrate 100 is positioned at the processing position in the process chamber 201, subsequently, film formation is performed by the substrate processing apparatus 200. The film formation is to form the insulating film 110. Details of the film formation will be described later.

(Substrate Unloading)

After finishing the film formation, subsequently, substrate unloading is performed by the substrate processing apparatus 200, and the processed substrate 100 is unloaded from the container 202. Specifically, the temperature inside the container 202 is lowered to a temperature at which the substrate 200 can be unloaded, and the inside of the process chamber 201 is purged with $N_2$ gas as an inert gas, so that the pressure inside the container 202 is adjusted to a pressure at which the substrate can be transferred. After the pressure adjustment, the substrate support 210 is moved down and the substrate 100 is moved to the transfer space 206. Then, the gate valve 203 is opened, and the substrate 100 is unloaded from the container 202 through the substrate loading/unloading port 204.

(4) Specific Procedure of Film Formation

Next, a specific procedure for the above-described film formation in the substrate processing will be described.

Figure 5:
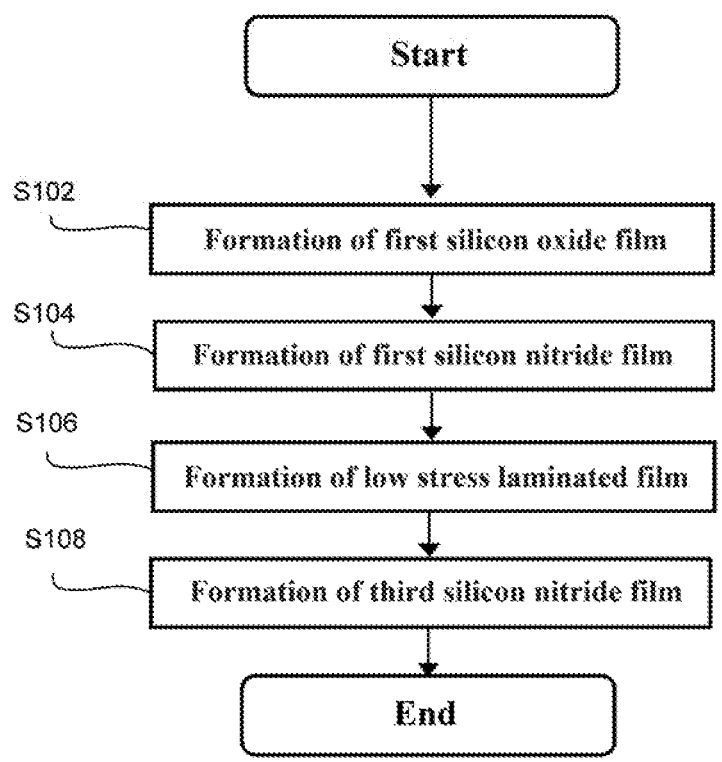
FIG. 5 is a flowchart illustrating a basic procedure of a film formation performed by the substrate processing apparatus according to an embodiment of the present disclosure.
Figure 6:
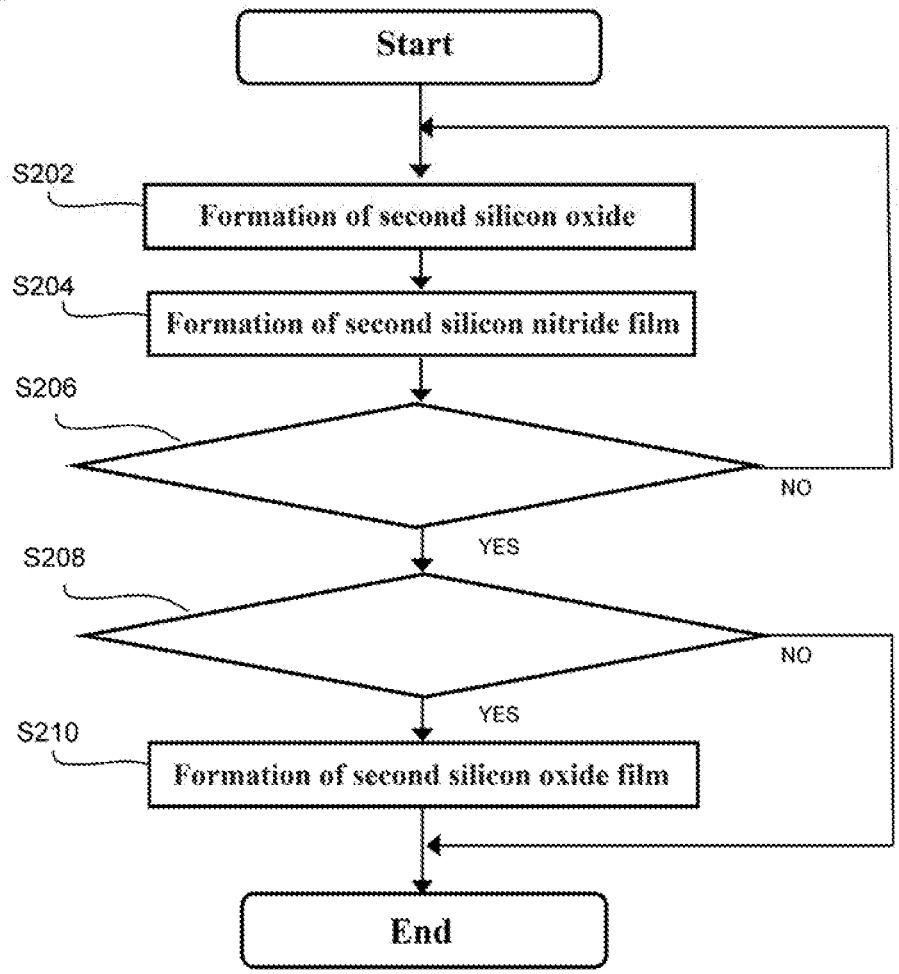
FIG. 6 is a flowchart illustrating a detailed procedure of a part of the film formation performed by the substrate processing apparatus according to an embodiment of the present disclosure.
Figure 7A:
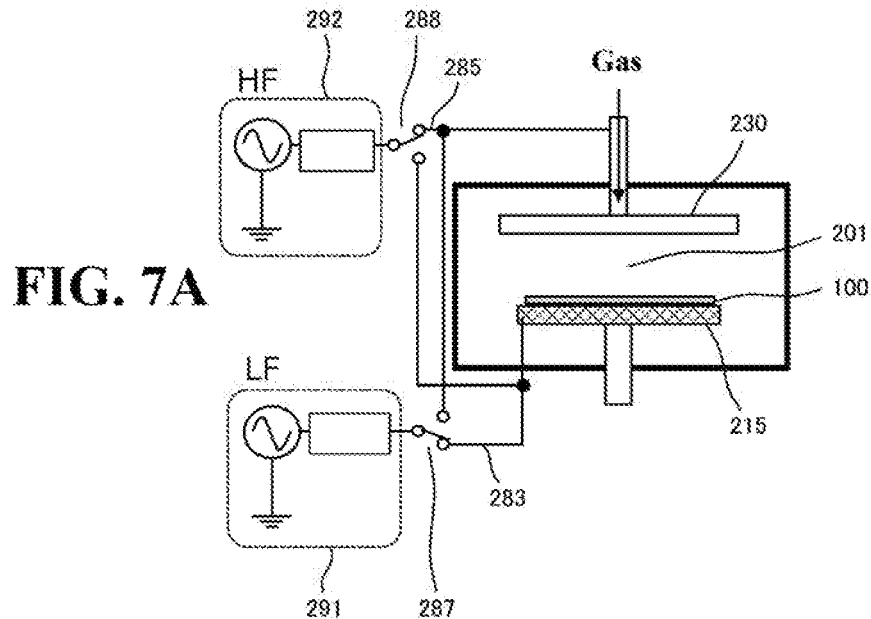
FIGS. 7A and 7B are explanatory views illustrating a specific mode of switching performed by the substrate processing apparatus in the film formation according to an embodiment of the present disclosure.
Figure 7B:
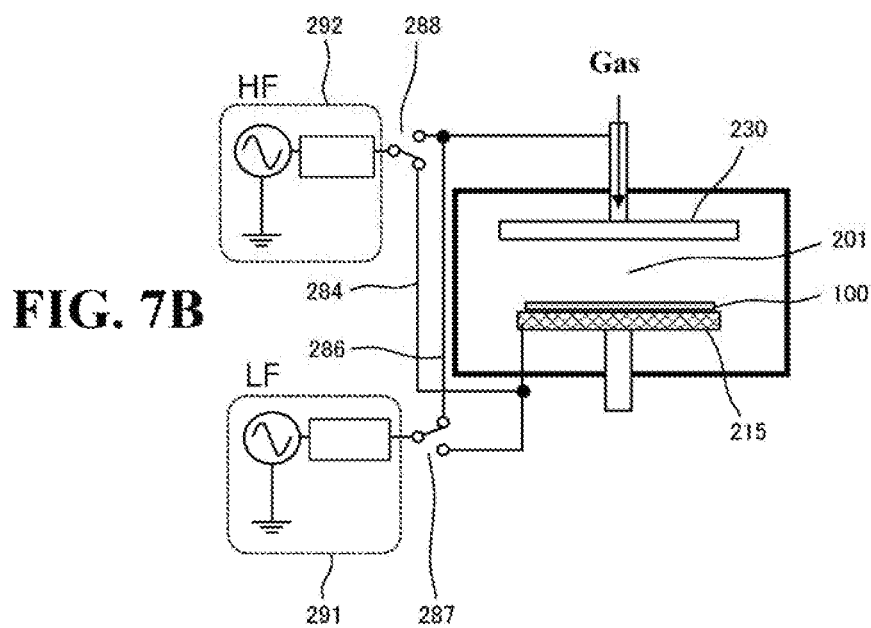

FIG. 5 is a flowchart illustrating a basic procedure of the film formation performed by the substrate processing apparatus according to an embodiment of the present disclosure, and FIG. 6 is a flowchart illustrating a detailed procedure of a part of the film formation performed by the substrate processing apparatus according to an embodiment of the present disclosure, and FIGS. 7A and 7B are explanatory views illustrating a specific mode of switching performed by the substrate processing apparatus in the film formation according to an embodiment of the present disclosure, and FIGS. 8A, 8B, 8C, 8D, 8E and 8F are side sectional views schematically illustrating a configuration example of the insulating film formed in the film formation performed by the substrate processing apparatus according to an embodiment of the present disclosure.

As illustrated in FIG. 5, the film formation for forming the insulating film 110 includes: formation of a first silicon oxide film (formation of a first silicon oxide film (S102)); formation of a first silicon nitride film (S104); formation of a low stress laminated film (S106); and formation of a third silicon nitride film (S108).

Further, as illustrated in FIG. 6, in the film formations, the formation of the low stress laminated film (S106) includes at least formation of a second silicon oxide film (S202) and formation of a second silicon nitride film (S204).

Each film formation will be sequentially described in detail hereafter.

(Formation of First Silicon Oxide Film: S102)

The formation of the first silicon oxide film (S102) is to perform processing for forming a SiO film 111 as a first silicon oxide film on the insulating film 109 in the substrate 100 which is the workpiece.

Therefore, in the formation of the first silicon oxide film (S102), for example, TEOS gas as silicon-containing gas is supplied from the first gas supplier 240 into the process chamber 201 through the shower head 230, and, for example, $O_2$ gas as oxygen-containing gas is supplied from the second gas supplier 250 into the process chamber 201 through the shower head 230. Thereby, the TEOS gas as the silicon-containing gas and the $O_2$ gas as the oxygen-containing gas are supplied into the process chamber 201.

Further, in the formation of the first silicon oxide film (S102), as illustrated in FIG. 7A, switching by the switch 288 is performed so that the high frequency power supplier 292 is connected to the wiring 285, and switching by the switch 287 is performed so that the low frequency power supplier 291 is connected to the wiring 283. Thereby, the high frequency power is supplied from the high frequency power supplier 292 to the shower head 230 as the top electrode, and the low frequency power is supplied from the low frequency power supplier 291 to the bottom electrode 215.

Figure 8A:
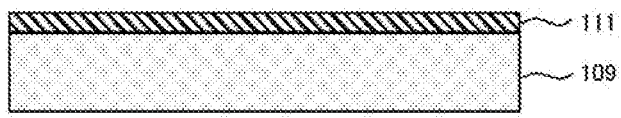
FIGS. 8A, 8B, 8C, 8D, 8E and 8F are side sectional views schematically illustrating a configuration example of the insulating film formed by the film formation performed by the substrate processing apparatus according to an embodiment of the present disclosure.

The TEOS gas and the $O_2$ gas supplied into the process chamber 201 are set in a plasma state by supplying electric power to the shower head 230 and the bottom electrode 215, and is applied and deposited to/on the insulating film 109 of the substrate 100 which is the workpiece. Thereby, as illustrated in FIG. 8A, the SiO film 111, which is the film containing Si element and O element, is formed as a first silicon oxide film on the insulating film 109 including SiN film.

At this time, the SiO film 111 is formed under a condition that high frequency power is applied to the shower head 230 and low frequency power is applied to the bottom electrode 215. That is, the processing gas for forming the SiO film 111 is set in a high density plasma state by the high frequency, and ions in the plasma are applied to the insulating film 109 of the substrate 100 by the low frequency. Therefore, Si element and O element are bonded at high density to form the SiO film 111, and meanwhile, impurity bonds such as Si—H bonds in which Si element and H element are bonded are broken by the low frequency. Accordingly, a film in which Si element and O element are densely arranged, that is, a dense SiO film 111 is formed on the insulating film 109.

(Formation of First Silicon Nitride Film: S104)

Formation of the first silicon nitride film (S104) performed after the formation of the first silicon oxide film (S102) is to perform processing for forming a SiN film 112 as a first silicon nitride film on the SiO film 111 formed in the formation of the first silicon oxide film (S102).

Therefore, in the formation of the first silicon nitride film (S104), for example, $SiH_4$ gas as a silicon-containing gas, is supplied from the first gas supplier 240 into the process chamber 201 through the shower head 230, and, for example, $NH_3$ gas, as a nitrogen-containing gas is supplied from the third gas supplier 260 into the process chamber 201 through the shower head 230. Thereby, the $SiH_4$ gas as the silicon-containing gas and the $NH_3$ gas as the oxygen-containing gas are supplied into the process chamber 201.

Further, in the formation of the first silicon nitride film (S104), as illustrated in FIG. 7A, switching by the switch 288 is performed so that the high frequency power supplier 292 is connected to the wiring 285, and switching by the switch 287 is performed so that the low frequency power supplier 291 is connected to the wiring 283. Thereby, the high frequency power is supplied from the high frequency power supplier 292 to the shower head 230 as the top electrode, and the low frequency power is supplied from the low frequency power supplier 291 to the bottom electrode 215.

Figure 8B:
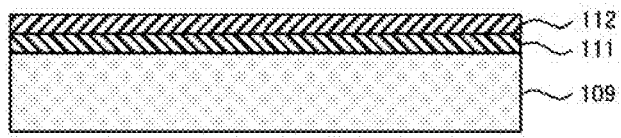

The $SiH_4$ gas and the $NH_3$ gas supplied into the process chamber 201 are set in a plasma state by supplying electric power to the shower head 230 and the bottom electrode 215, and is applied and deposited to/on the SiO film 111 of the substrate 100 which is the workpiece. Thereby, as illustrated in FIG. 8B, the SiN film 112, which is the film containing Si element and N element, is formed as a first silicon nitride film on the SiO film 111.

At this time, the SiN film 112 is formed under the condition that high frequency power is applied to the shower head 230 and low frequency power is applied to the bottom electrode 215. That is, the processing gas for forming the SiN film 112 is set in a high density plasma state by the high frequency, and ions in the plasma are applied to the SiO film 111 of the substrate 100 by the low frequency. Therefore, the Si element and the N element are bonded at high density to form the SiN film 112, and meanwhile, impurity bonds such as Si—H bonds in which Si element and H element are bonded are broken by the low frequency. Accordingly, a film in which Si element and N element are densely arranged, that is, a dense SiN film 112 is formed on the SiO film 111.

(Formation of Second Silicon Oxide Film: S202)

Formation of the second silicon oxide film (S202) performed after the formation of the first silicon nitride film (S104) is to perform processing for forming a SiO film 113 as the second silicon oxide film on the SiN film 112 formed in the formation of the first silicon nitride film (S104).

Therefore, in the formation of the second silicon oxide film (S202), for example, TEOS gas as the silicon-containing gas is supplied from the first gas supplier 240 into the process chamber 201 through the shower head 230, and, for example, $O_2$ gas as the oxygen-containing gas is supplied from the second gas supplier 250 into the process chamber 201 through the shower head 230. Thereby, the TEOS gas as the silicon-containing gas and the $O_2$ gas as the oxygen-containing gas are supplied into the process chamber 201.

Further, in the formation of the second silicon oxide film (S202), as illustrated in FIG. 7B, switching by the switch 288 is performed so that the high frequency power supplier 292 is connected to the wiring 284, and switching by the switch 287 is performed so that the low frequency power supplier 291 is connected to the wiring 286. Thereby, the high frequency power is supplied from the high frequency power supplier 292 to the bottom electrode 215, and the low frequency power is supplied from the low frequency power supplier 291 to the shower head 230 as the top electrode.

Figure 8C:
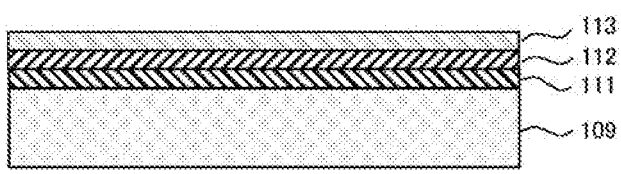

The TEOS gas and the $O_2$ gas supplied into the process chamber 201 are set in a plasma state by supplying electric power to the shower head 230 and the bottom electrode 215, and is applied and deposited to/on the SiN film 112 of the substrate 100 which is the workpiece. Thereby, as illustrated in FIG. 8C, the SiO film 113, which is the film containing Si element and O element, is formed as the second silicon oxide film on the SiN film 112.

Contrary to the case of the formation of the first silicon oxide film (S102), the SiO film 113 is formed under a condition that low frequency power is applied to the shower head 230 and high frequency power is applied to the bottom electrode 215. Therefore, the SiO film 113 is formed as a SiO film 113 in which an arrangement of Si element and O element is rough and an internal stress is relaxed, compared with the SiO film 111 as the first silicon oxide film.

(Formation of Second Silicon Nitride Film: S204)

Formation of the second silicon nitride film (S204) performed after the formation of the second silicon oxide film (S202) is to perform processing for forming a SiN film 114 as a second silicon nitride film on the SiO film 113 formed in the formation of the second silicon oxide film (S202).

Therefore, in the formation of the second silicon nitride film (S204), for example, $SiH_4$ gas is supplied as the silicon-containing gas from the first gas supplier 240 into the process chamber 201 through the shower head 230, and for example, $NH_3$ gas is supplied as the nitrogen-containing gas from the third gas supplier 260 into the process chamber 201 through the shower head 230. Thereby, $SiH_4$ gas as silicon-containing gas and $NH_3$ gas as oxygen-containing gas are supplied into the process chamber 201.

Further, in the formation of the second silicon nitride film (S204), as illustrated in FIG. 7B, switching by the switch 288 is performed so that the high frequency power supplier 292 is connected to the wiring 284, and switching by the switch 287 is performed so that the low frequency power supplier 291 is connected to the wiring 286. Thereby, the high frequency power is supplied from the high frequency power supplier 292 to the bottom electrode 215, and the low frequency power is supplied from the low frequency power supplier 291 to the shower head 230 as the top electrode.

Figure 8D:
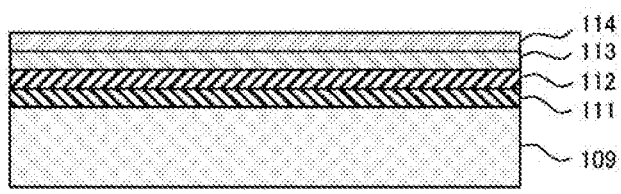

The $SiH_4$ gas and the $NH_3$ gas supplied into the process chamber 201 are set in a plasma state by supplying electric power to the shower head 230 and the bottom electrode 215, and is applied and deposited to/on the SiO film 113 of the substrate 100 which is the workpiece. Thereby, as illustrated in FIG. 8D, the SiN film 114, which is the film containing Si element and N element, is formed as the second silicon nitride film on the SiO film 113.

Contrary to the case of the formation of the first silicon nitride film (S104), the SiN film 114 is formed under a condition that low frequency power is applied to the shower head 230 and high frequency power is applied to the bottom electrode 215. Therefore, the SiO film 114 is formed as the SiO film 114 in which an arrangement of Si element and O element is rough and an internal stress is relaxed, compared with the SiO film 112 as the first silicon nitride film.

(Formation of Low Stress Laminated Film: S106)

In the formation of the low stress laminated film (S106) including the formation of the second silicon oxide film (S202) and the formation of the second silicon nitride film (S204) described above, as illustrated in FIG. 6, after end of each of the film formations (S202, S204), it is determined whether each of these film formations (S202, S204) has been performed a predetermined number of times (for example, 2 to 5 times) (S206). Then, each of these film formations (S202, S204) is repeatedly performed until it is performed a predetermined number of times.

After performing each film formation (S202, S204) a predetermined number of times, it is determined whether an uppermost layer (for example, SiN film 114) of the laminated film obtained by repeating each film formation (S202, S204) has the same composition as the composition of a protective film that covers the uppermost layer (specifically, SiN film 116 formed in formation of a third silicon nitride film (S108) described later) (S208). Then, when the compositions are the same, the formation of the second silicon oxide film (S210) is performed again so as to make the compositions different. In the formation of the second silicon oxide film (S210), the same processing as in the above-described formation of the second silicon oxide film (S202) is performed.

Figure 8E:
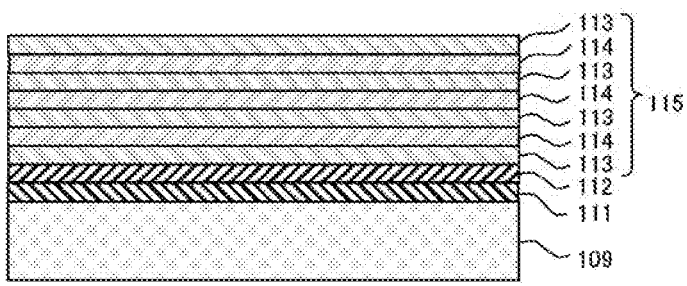

Thereby, as illustrated in FIG. 8E, a laminated film formed by laminating the SiO film 113 and the SiN film 114 is formed as a low stress laminated film 115 on the SiN film 112.

(Formation of Third Silicon Nitride Film: S108)

Formation of a third silicon nitride film (S108) performed after the formation of the low stress laminated film (S106) is to perform processing for forming the SiN film 116 as the third silicon nitride film on the low stress laminated film 115 formed in the formation of the low stress laminated film (S106).

Therefore, in the formation of the third silicon nitride film (S108), for example, $SiH_4$ gas as the silicon-containing gas is supplied from the first gas supplier 240 into the process chamber 201 through the shower head 230, and for example, $NH_3$ gas as the nitrogen-containing gas is supplied from the third gas supplier 260 into the process chamber 201 through the shower head 230. Thereby, the $SiH_4$ gas as the silicon-containing gas and the $NH_3$ gas as the oxygen-containing gas are supplied into the process chamber 201.

Further, in the formation of the third silicon nitride film (S108), as illustrated in FIG. 7A, switching by the switch 288 is performed so that the high frequency power supplier 292 is connected to the wiring 285, and switching by the switch 287 is performed so that the low frequency power supplier 291 is connected to the wiring 283. Thereby, the high frequency power is supplied from the high frequency power supplier 292 to the shower head 230 as the top electrode, and the low frequency power is supplied from the low frequency power supplier 291 to the bottom electrode 215.

Figure 8F:
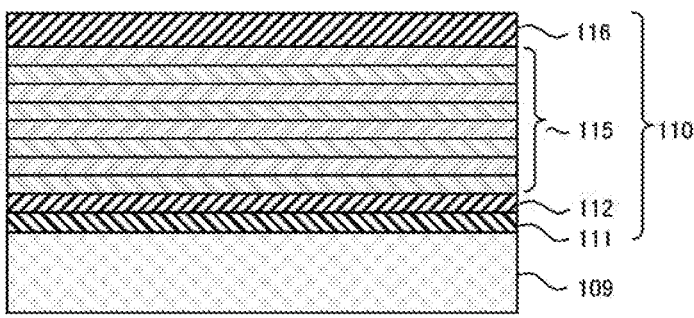

The $SiH_4$ gas and the $NH_3$ gas supplied into the process chamber 201 are set in a plasma state by supplying electric power to the shower head 230 and the bottom electrode 215, and is applied and deposited to/on the low stress laminated film 115 of the substrate 100 which is the workpiece. Thereby, as illustrated in FIG. 8F, SiN film 116, which is a film containing Si element and N element, is formed as a third silicon nitride film on the low stress laminated film 115.

In this way, the SiN film 116 is formed so as to cover the uppermost layer of the low stress laminated film 115. Therefore, it is preferable that the SiN film 116 be capable of exhibiting a sufficient function as a protective film for the low stress laminated film 115.

In this regard, the SiN film 116 is formed under a condition that high frequency power is applied to the shower head 230 and low frequency power is applied to the bottom electrode 215, and therefore is formed as a film in which Si element and N element are densely arranged, that is, a dense SiN film 116. Accordingly, the SiN film 116 is very suitable for functioning as a protective film.

Further, since the SiN film 116 functions as a protective film, the SiN film is preferable for improving a margin of protection performance as long as it is formed to be thicker than the other SiO films 111, 113 and SiN films 112, 114, etc.

By sequentially performing the formation of the first silicon oxide film (S102), the formation of the first silicon nitride film (S104), the formation of the low stress laminated film (S106), and the formation of the third silicon nitride film (S108) as described above, as illustrated in FIG. 8F, a laminate of the SiN film 116 and the low stress laminated film 115 formed by laminating the SiO film 111, SiN film 112, SiO film 113 and SiN film 114, is formed as the insulating film 110 on the insulating film 109.

In this way, the insulating film 110 is formed by laminating the SiO films 111, 113 and the SiN films 112, 114. It is generally known that the SiO film has a high compressive stress and the SiN film has a high tensile stress. That is, the SiO film and the SiN film have opposite characteristics regarding membrane stress. Accordingly, the insulating film 110 acts so that the characteristics of the SiO films 111 and 113 and the characteristics of the SiN films 112 and 114 cancel each other, and has excellent resistance to vibration.

In addition, the insulating film 110 is formed by laminating the dense SiO film 111 and SiN film 112, and the SiO film 113 and SiN film 114 which are coarser than the above SiO film 111 and SiN film 112 and have relaxed internal stress. Accordingly, since the insulating film 110 has a laminated portion in which the internal stress is relaxed, it has extremely excellent resistance to vibration.

(5) Effects of the Present Embodiment

According to the present embodiments, one or more of the following effects are exhibited.

(a) In the present embodiment, the film formation in processing the substrate includes, at least: the formation of the first silicon oxide film (S102), the formation of the first silicon nitride film (S104), the formation of the second silicon oxide film (S202), and the formation of the second silicon nitride film (S204). Then, in the formation of the first silicon oxide film (S102), silicon-containing gas and oxygen-containing gas are supplied to the process chamber 201, and switching by the switches 287 and 288 is performed so that high frequency power is supplied to the shower head 230 and low frequency power is supplied to the bottom electrode 215. Further, in the formation of the first silicon nitride film (S104), silicon-containing gas and nitrogen-containing gas are supplied to the process chamber 201, and switching by the switches 287 and 288 is performed so that high frequency power is supplied to the shower head 230 and low frequency power is supplied to the bottom electrode 215. Further, in the formation of the second silicon oxide film (S202), silicon-containing gas and oxygen-containing gas are supplied to the process chamber 201, and switching by the switches 287 and 288 is performed so that low frequency power is supplied to the shower head 230 and high frequency power is supplied to the bottom electrode 215. Further, in the formation of the second silicon nitride film (S204), silicon-containing gas and nitrogen-containing gas are supplied to the process chamber 201, and switching by the switches 287 and 288 is performed so that low frequency power is supplied to the shower head 230 and high frequency power is supplied to the bottom electrode 215.

Therefore, according to the present embodiment, the SiO films 111, 113 and the SiN films 112, 114 are laminated to form the insulating film 110, and the insulating film 110 having excellent resistance to vibration can be formed. In addition, the insulating film 110 is formed by laminating dense SiO film 111 and SiN film 112, and SiO film 113 and SiN film 114 which are coarser than the above SiO film 111 and SiN film 112 and in which an arrangement of Si element and O element is rough and an internal stress is relaxed, and therefore has extremely excellent resistance to vibration.

Namely, according to the present embodiment, by switching the frequency of the electric power applied to the shower head 230 and the bottom electrode 215 by using the switches 287 and 288, the laminated film formed in the film formation can be adjusted in a wide range of compressive stress and tensile stress. This realizes an appropriate combination of the membrane stresses in each film that configures the laminated film, and this means that a film forming technique is provided, which is capable of forming a film having extremely excellent resistance to vibration.

The film forming technique according to the present embodiment is particularly effective when applied to a semiconductor device having a vibratable insulating film, and specifically, as described in the present embodiment, it is very effective when applied to the membrane structure of the CMUT device.

The membrane structure of the CMUT device is configured to vibrate a vibrating film. Therefore, as long as the vibrating film has extremely excellent resistance to vibration, deterioration of the membrane structure due to the vibration can be suppressed even if the vibrating film repeatedly vibrates many times. When the deterioration of the membrane structure can be suppressed, an occurrence of defects in the CMUT device such as conduction between electrodes due to bending of the vibrating film can be suppressed.

The bending resistance of the membrane structure of the CMUT device is more excellent than constituent films of other semiconductor devices such as NAND type memory. From this point as well, the film forming technique according to the present embodiment is very effective when applied to the membrane structure of the CMUT device.

(b) In the present embodiment, the formation of the second silicon oxide film (S202) and the formation of the second silicon nitride film (S204) are repeated a plurality of number of times until being performed a preset predetermined number of times, to thereby form the low stress laminated film 115. The low stress laminated film 115 is the laminated film of the SiO film 113 and the SiN film 114 in which the internal stress is relaxed.

Therefore, according to the present embodiment, the proportion of the low stress laminated film 115 in the insulating film 110 increases, and therefore the resistance of the insulating film 110 to vibration can be further improved.

(c) In the present embodiment, the formation of the third silicon nitride film (S108) is provided, separately from the formation of the first silicon nitride film (S104) and the formation of the second silicon nitride film (S204). Then, in the formation of the third silicon nitride film (S108), silicon-containing gas and nitrogen-containing gas are supplied to the process chamber 201 and switching by the switches 287 and 288 is performed so that high frequency power is supplied to the shower head 230 and low frequency power is supplied to the bottom electrode 215.

Therefore, according to the present embodiment, the dense SiN film 116 can be formed as a protective film covering the uppermost layer. Accordingly, the SiN film is very suitable for functioning as a protective film. To improve the margin of protection performance, the SiN film 116 is preferably formed to be thicker than the other SiO films 111 and 113, the SiN films 112 and 114, and the like.

(d) In the present embodiment, after etching away the sacrificial layer for forming the cavity 107 of the CMUT device through the hole 130 provided in the insulating films 106 and 109 which are coating films for covering the sacrificial layer, the hole 130 is sealed by performing the film formation of forming the insulating film 110 on the insulating film 109. Then, the film formation of forming the insulating film 110 sequentially undergoes at least the formation of the first silicon oxide film (S102), the formation of the first silicon nitride film (S104) and the formation of the low stress laminated film (S106).

Therefore, according to the present embodiment, since the insulating film 110 that seals the hole 130 is formed by a multi-divided deposition method, the hole 130 can be easily and surely sealed as compared with a case of a non-divided deposition method. Further, the multi-divided deposition method makes it easier to cope with an increase in film thickness. That is, according to the present embodiment, the multi-divided deposition method makes it easier to cope with the increase in film thickness while sufficiently ensuring embedding property for the hole 130.

Other Embodiments

Although one embodiment of the present disclosure has been specifically described above, the present disclosure is not limited to the above-described embodiment, and various modifications can be made without departing from the scope of the disclosure.

In the embodiments described above, the case where the semiconductor device is the CMUT device has been described as an example, but the present disclosure is not limited thereto. That is, the present disclosure is applicable to the manufacture of a semiconductor device having a vibratable insulating film, and may be applied to other than the CMUT device.

Further, in the above-described embodiment, explanation is given for a case of sequentially laminating the SiO film 111 as the first silicon oxide film, the SiN film 112 as the first silicon nitride film, the SiO film 113 as the second silicon oxide film, and the SiN film 114 as the second silicon nitride film, as an example. However, the present disclosure is not limited thereto. That is, a laminating order of these films 111 to 114 is not particularly limited, and the laminating order different from that of the above-described embodiment may be replaced.

<Preferable Aspects of the Present Disclosure>

Preferable aspects of the present disclosure will be supplementarily described hereafter.

[Supplementary Description 1]

According to an aspect of the present disclosure, there is provided a method for manufacturing a semiconductor device having a vibratable insulating film, the method including at least:

forming a first silicon oxide film;
forming a first silicon nitride film;
forming a second silicon oxide film; and
forming a second silicon nitride film,
as a formation of the insulating film, each film formation being performed using a substrate processing apparatus configured to supply gas to a process chamber including a top electrode and a bottom electrode, and selectively supply either high-frequency power or low-frequency power to each of the top electrode and the bottom electrode by switching, and the formation of the first silicon oxide film including:

supplying silicon-containing gas and oxygen-containing gas to the process chamber, and performing switching to supply high frequency power to the top electrode, and supply low frequency power to the bottom electrode, and the formation of the first silicon nitride film including:

supplying silicon-containing gas and nitrogen-containing gas to the process chamber, and performing switching to supply high frequency power to the top electrode and supply low frequency power to the bottom electrode, the formation of the second silicon oxide film including:

supplying silicon-containing gas and nitrogen-containing gas to the process chamber, and performing switching to supply low frequency power to the top electrode and supply high frequency power to the bottom electrode, the formation of the second silicon nitride film including:

supplying silicon-containing gas and nitrogen-containing gas to the process chamber, and performing switching to supply low frequency power to the top electrode and supply high frequency power to the bottom electrode.

[Supplementary Description 2]

Preferably, there is provided the method according to the supplementary description 1, wherein the formation of the second silicon oxide film and the formation of the second silicon nitride film are repeated a plurality of number of times.

[Supplementary Description 3]

Preferably, there is provided the method according to the supplementary description 1 or 2, including:

forming a third silicon nitride film as the formation of the insulating film, separately from the formation of the first silicon nitride film and the formation of the second silicon nitride film, the formation of the third silicon nitride film including:

supplying silicon-containing gas and nitrogen-containing gas to the process chamber, and performing switching to supply high frequency power to the top electrode and supply low frequency power to the bottom electrode.

[Supplementary Description 4]

Preferably, there is provided the method according to any one of the supplementary descriptions 1 to 3, wherein after removing away a sacrificial layer formed to enable the insulating film to vibrate, through a hole provided in a coating film covering the sacrificial layer, the formation of the insulating film on the coating film is performed to seal the hole.

[Supplementary Description 5]

According to other aspect of the present disclosure, there is provided a substrate processing apparatus, including:

a process chamber that houses a workpiece;
a first gas supplier that supplies silicon-containing gas to the process chamber;
a second gas supplier that supplies oxygen-containing gas to the process chamber;
a third gas supplier that supplies nitrogen-containing gas to the process chamber;
a top electrode and a bottom electrode disposed in the process chamber;
a high frequency power supplier that supplies high frequency power to the top electrode or the bottom electrode;
a low frequency power supplier that supplies low frequency power to the top electrode or the bottom electrode;
a switch that selects whether to supply high frequency power from the high frequency power supplier or low frequency power from the low frequency power supplier to each of the top electrode and the bottom electrode; and
a controller that controls supply of gas by the first gas supplier, the second gas supplier, and the third gas supplier, and controls selective switching of power supply by the switch, and configured to perform at least:

processing for forming a first silicon oxide film that configures an insulating film, by supplying silicon-containing gas and oxygen-containing gas to the process chamber, and performing switching to supply high frequency power to the top electrode and supply low frequency power to the bottom electrode;

processing for forming a first silicon nitride film that configures the insulating film, by supplying silicon-containing gas and nitrogen-containing gas to the process chamber, and performing switching to supply high frequency power to the top electrode and supply low frequency power to the bottom electrode;

processing for forming a second silicon oxide film that configures the insulating film, by supplying silicon-containing gas and oxygen-containing gas to the process chamber, and performing switching to supply low frequency power to the top electrode and supply high frequency power to the bottom electrode; and processing for forming a second silicon nitride film that configures the insulating film, by supplying silicon-containing gas and oxygen-containing gas to the process chamber, and performing switching to supply low frequency power to the top electrode and supply high frequency power to the bottom electrode, when forming a vibratable insulating film on the workpiece.

[Supplementary Description 6]

According to further other aspect of the present disclosure, there is provided a program for causing a substrate processing apparatus to execute by a computer at least a procedure for forming a first silicon oxide film, a procedure for forming a first silicon nitride film, a procedure for forming a second silicon oxide film, and a procedure for forming a second silicon nitride film as procedures for forming a vibratable insulating film, the procedure for forming the first silicon oxide film including:

supplying silicon-containing gas and oxygen-containing gas to the process chamber, and performing switching to supply high frequency power to a top electrode and supply low frequency power to a bottom electrode, the procedure for forming the first silicon nitride film including:
supplying silicon-containing gas and nitrogen-containing gas to the process chamber, and performing switching to supply high frequency power to the top electrode and low frequency power to the bottom electrode,
the procedure for forming the second silicon oxide film including:
supplying silicon-containing gas and oxygen-containing gas to the process chamber, and performing switching to supply low frequency power to the top electrode and supply high frequency power to the bottom electrode, and
the procedure for forming the second silicon nitride film including:
supplying silicon-containing gas and nitrogen-containing gas to the process chamber, and performing switching to supply low frequency power to the top electrode and supply high frequency power to the bottom electrode,
using the substrate processing apparatus configured to supply gas to the process chamber including the top electrode and the bottom electrode, and selectively supply either high-frequency power or low-frequency power to each of the top electrode and the bottom electrode by switching.

[Supplementary Description 7]

According to further other aspect of the present disclosure, there is provided a non-transitory computer readable recording medium storing a program that causes, by a computer, a substrate processing apparatus to perform a process comprising, at least a procedure for forming a first silicon oxide film, a procedure for forming a first silicon nitride film, a procedure for forming a second silicon oxide film, and a procedure for forming a second silicon nitride film as procedures for forming a vibratable insulating film,
the procedure for forming the first silicon oxide film including:
supplying silicon-containing gas and a nitrogen-containing gas to the process chamber, and performing switching to supply high frequency power to a top electrode and supply low frequency power to a bottom electrode,
the procedure for forming the first silicon nitride film including:
supplying silicon-containing gas and nitrogen-containing gas to the process chamber, and performing switching to supply high frequency power to the top electrode and low frequency power to the bottom electrode,
the procedure for forming the second silicon oxide film including:
supplying silicon-containing gas and oxygen-containing gas to the process chamber, and performing switching to supply low frequency power to the top electrode and supply high frequency power to the bottom electrode, and
the procedure for forming the second silicon nitride film including:
supplying silicon-containing gas and nitrogen-containing gas to the process chamber, and performing switching to supply low frequency power to the top electrode and supply high frequency power to the bottom electrode,
using the substrate processing apparatus configured to supply gas to the process chamber including the top electrode and the bottom electrode, and selectively supply either high-frequency power or low-frequency power to each of the top electrode and the bottom electrode by switching.

DESCRIPTION OF SIGNS AND NUMERALS

100 Substrate
104 Bottom electrode
107 Cavity
106, 109, 110 Insulating film
108 Top electrode
111 SiO film (first silicon oxide film)
112 SiN film (first silicon nitride film)
113 SiO film (second silicon oxide film)
114 SiN film (second silicon nitride film)
115 Low stress laminated film
116 SiN film (third silicon nitride film)
130 Hole
200 Substrate processing apparatus
201 Process chamber
215 Bottom electrode
230 Shower head (top electrode)
240 First gas supplier
250 Second gas supplier
260 Third gas supplier
287, 288 Switch
291 Low frequency power supplier
292 High frequency power supplier
400 Controller

The invention claimed is:

1. A method for manufacturing a semiconductor device having a vibratable insulating film, the method comprising at least:
forming a first silicon oxide film;
forming a first silicon nitride film;
forming a second silicon oxide film; and
forming a second silicon nitride film,
as a formation of the insulating film,
the formation of the second silicon oxide film comprising:
supplying silicon-containing gas and oxygen-containing gas to a process chamber, and performing switching to supply low frequency power to a top electrode installed in the process chamber, and supply high frequency power to a bottom electrode installed in the process chamber, and
the formation of the second silicon nitride film comprising:
supplying silicon-containing gas and nitrogen-containing gas to the process chamber, and performing switching to supply low frequency power to the top electrode and supply high frequency power to the bottom electrode.

2. The method according to claim 1,
wherein the formation of the first silicon oxide film comprises:
supplying silicon-containing gas and oxygen-containing gas to the process chamber, and performing switching to supply high frequency power to the top electrode and supply low frequency power to the bottom electrode, and
the formation of the first silicon nitride film comprises:
supplying silicon-containing gas and nitrogen-containing gas to the process chamber, and performing switching to supply high frequency power to the top electrode and supply low frequency power to the bottom electrode.

3. The method according to claim 2, wherein the formation of the second silicon oxide film and the formation of the second silicon nitride film are repeated a plurality of number of times.

4. The method according to claim 3, comprising:
forming a third silicon nitride film as the formation of the insulating film, separately from the formation of the first silicon nitride film and the formation of the second silicon nitride film,
the formation of the third silicon nitride film comprising: supplying silicon-containing gas and nitrogen-containing gas to the process chamber, and performing switching to supply high frequency power to the top electrode and supply low frequency power to the bottom electrode.

5. The method according to claim 4, wherein when the formation of the second silicon oxide film and the formation of the second silicon nitride film are repeated a plurality of number of times, and when an uppermost layer has the same composition as the third silicon nitride film, the formation of the second silicon oxide film is performed to make each composition different.

6. The method according to claim 5, wherein after removing away a sacrificial layer formed to enable the insulating film to vibrate, through a hole provided in a coating film covering the sacrificial layer, a formation of the insulating film on the coating film is performed to seal the hole.

7. The method according to claim 4, wherein after removing away a sacrificial layer formed to enable the insulating film to vibrate, through a hole provided in a coating film covering the sacrificial layer, a formation of the insulating film on the coating film is performed to seal the hole.

8. The method according to claim 3, wherein after removing away a sacrificial layer formed to enable the insulating film to vibrate, through a hole provided in a coating film covering the sacrificial layer, a formation of the insulating film on the coating film is performed to seal the hole.

9. The method according to claim 2, wherein after removing away a sacrificial layer formed to enable the insulating film to vibrate, through a hole provided in a coating film covering the sacrificial layer, the formation of the insulating film on the coating film is performed to seal the hole.

10. The method according to claim 1, wherein the formation of the second silicon oxide film and the formation of the second silicon nitride film are repeated a plurality of number of times.

11. The method according to claim 10, comprising:
forming a third silicon nitride film as the formation of the insulating film, separately from the formation of the first silicon nitride film and the formation of the second silicon nitride film,
the formation of the third silicon nitride film comprising: supplying silicon-containing gas and nitrogen-containing gas to the process chamber, and performing switching to supply high frequency power to the top electrode and supply low frequency power to the bottom electrode.

12. The method according to claim 11, wherein when the formation of the second silicon oxide film and the formation of the second silicon nitride film are repeated a plurality of number of times, and when an uppermost layer has the same composition as the third silicon nitride film, the formation of the second silicon oxide film is performed to make each composition different.

13. The method according to claim 11, wherein after removing away a sacrificial layer formed to enable the insulating film to vibrate, through a hole provided in a coating film covering the sacrificial layer, the formation of the insulating film on the coating film is performed to seal the hole.

14. The method according to claim 10, wherein after removing away a sacrificial layer formed to enable the insulating film to vibrate, through a hole provided in a coating film covering the sacrificial layer, the formation of the insulating film on the coating film is performed to seal the hole.

15. The method according to claim 1, comprising:
forming a third silicon nitride film as the formation of the insulating film, separately from the formation of the first silicon nitride film and the formation of the second silicon nitride film,
the formation of the third silicon nitride film comprising: supplying silicon-containing gas and nitrogen-containing gas to the process chamber, and performing switching to supply high frequency power to the top electrode and supply low frequency power to the bottom electrode.

16. The method according to claim 15, wherein when the formation of the second silicon oxide film and the formation of the second silicon nitride film are repeated a plurality of number of times, and when an uppermost layer has the same composition as the third silicon nitride film, the formation of the second silicon oxide film is performed to make each composition different.

17. The method according to claim 15, wherein after removing away a sacrificial layer formed to enable the insulating film to vibrate, through a hole provided in a coating film covering the sacrificial layer, the formation of the insulating film on the coating film is performed to seal the hole.

18. The method according to claim 1, wherein after removing away a sacrificial layer formed to enable the insulating film to vibrate, through a hole provided in a coating film covering the sacrificial layer, the formation of the insulating film on the coating film is performed to seal the hole.

19. A substrate processing apparatus, comprising:
a process chamber that houses a workpiece;
a first gas supplier that supplies silicon-containing gas to the process chamber;
a second gas supplier that supplies oxygen-containing gas to the process chamber;
a third gas supplier that supplies nitrogen-containing gas to the process chamber;
a top electrode and a bottom electrode disposed in the process chamber;
a high frequency power supplier that supplies high frequency power to the top electrode or the bottom electrode;
a low frequency power supplier that supplies low frequency power to the top electrode or the bottom electrode;
a switch that selects whether to supply high frequency power from the high frequency power supplier or low frequency power from the low frequency power supplier to each of the top electrode and the bottom electrode; and
a controller that controls supply of gas by the first gas supplier, the second gas supplier, and the third gas supplier, and controls selective switching of power supply by the switch,
and configured to perform at least:
processing for forming a second silicon oxide film that configures an insulating film, by supplying silicon-containing gas and oxygen-containing gas to the process chamber, and performing switching to supply low frequency power to the top electrode and supply high frequency power to the bottom electrode; and
processing for forming a second silicon nitride film that configures the insulating film, by supplying silicon-containing gas and nitrogen-containing gas to the process chamber, and performing switching to supply low frequency power to the top electrode and supply high frequency power to the bottom electrode, when forming a vibratable insulating film having the first silicon oxide film, the first silicon nitride film, the second silicon oxide film, and the second silicon nitride film on the workpiece.

20. A non-transitory computer readable recording medium storing a program that causes, by a computer, a substrate processing apparatus to perform a process comprising, at least a procedure for forming a first silicon oxide film, a procedure for forming a first silicon nitride film, a procedure for forming a second silicon oxide film, and a procedure for forming a second silicon nitride film as procedures for forming a vibratable insulating film, the procedure for forming the second silicon oxide film including: supplying silicon-containing gas and oxygen-containing gas to a process chamber, and performing switching to supply low frequency power to a top electrode installed in the process chamber and supply high frequency power to a bottom electrode installed in the process chamber, and the procedure for forming the second silicon nitride film including: supplying silicon-containing gas and nitrogen-containing gas to the process chamber and performing switching to supply low frequency power to the top electrode and supply high frequency power to the bottom electrode.

* * * * *